United States Patent [19]
Yanai et al.

[11] Patent Number: 5,846,562
[45] Date of Patent: Dec. 8, 1998

[54] ORAL COMPOSITION OF FUMAGILLOL DERIVATIVE

[75] Inventors: Shigeo Yanai, Himeji; Katsuichi Sudo, Takatsuki; Yohko Akiyama, Ohmihachiman; Naoki Nagahara, Itami, all of Japan

[73] Assignee: Takeda Chemical Industries, Ltd., Osaka, Japan

[21] Appl. No.: 831,490

[22] Filed: Mar. 28, 1997

[30] Foreign Application Priority Data

| Apr. 1, 1996 | [JP] | Japan | 8-078896 |
| Jun. 20, 1996 | [JP] | Japan | 8-159654 |
| Jul. 17, 1996 | [JP] | Japan | 8-187387 |

[51] Int. Cl.⁶ ........................ A61K 9/48
[52] U.S. Cl. .............. 424/451; 424/439; 424/463; 424/489; 514/475
[58] Field of Search .................. 424/438–439, 424/451, 452, 455–465, 474, 475–482, 489–502

[56] References Cited

FOREIGN PATENT DOCUMENTS 0 415 294 A2  3/1991  European Pat. Off. .

OTHER PUBLICATIONS

Copy of European Search Report mailed Jul. 14, 1997.

*Primary Examiner*—Neil S. Levy
*Attorney, Agent, or Firm*—David G. Conlin; David S. Resnick; Dike, Bronstein, Roberts & Cushman, LLP

[57] ABSTRACT

The present invention relates to a pharmaceutical composition for oral administration in which a fumagillol derivative is stabilized and exhibits remarkable antiangiogenesis activity in oral administration.

28 Claims, No Drawings

ORAL COMPOSITION OF FUMAGILLOL DERIVATIVE

FIELD OF THE INVENTION

The present invention relates to a pharmaceutical composition for a fumagillol derivative, a medicinally useful angiogenesis-inhibitor, wherein the fumagillol derivative is stable due to less decomposition by gastric acid in oral administration.

BACKGROUND OF THE INVENTION

Angiogenesis is the formation of new vessels at the capillary level. It has become clear that angiogenesis is closely associated with diseases such as cancer, diabetic retinopathy, and rheumatoid arthritis and the like. Since angiogenesis inhibitory substances do not act directly on the disease but suppresse the supply of blood by inhibiting development or growth of blood vessels, it can be a therapeutic (treating) agent for such angiogenesis-associating diseases based on a mechanism of action which is different from that of conventional ones. Particularly because angiogenesis is essential to the growth of solid tumors to supply nutrient therefor, there is great expectations that angiogenesis inhibitors will be applicable as antineoplastic drugs.

As a result of screening angiogenesis inhibitory substance, fumagillol derivatives have been founded. Examples of them are disclosed in, inter alia, EP-A-359,036 (JP-A-3-7270), EP-A-357,061 (JP-A-3-7222), EP-A-354,787, EP-A-386,667 (JP-A-3-14571), EP-A-387,650 (JP-A-3-7271), and EP-A-415,294 (JP-A-3-279376).

Further, EP-A-461427 discloses a complex of a fumagillol derivative or a salt thereof with an optionally esterified cyclodextrin, and an antineoplastic agent containing the complex.

EP-A-470,569 (JP-A-5-969) discloses a intravascular embolizing agent comprising a fumagillol derivative as an angiogenosis-inhibiting agent, and a intravascular embolizing substance such as wax (e.g. fatty acid glycerin ester).

EP-A-602,586 (JP-A-6-234631) discloses a pharmaceutical composition having improved stability comprising a fumagillol derivative and a fatty acid ester of glycerin or polyglycerin. The composition is a sustained-release composition and prevents decomposition of the fumagillol derivative during storage.

Angiogenesis inhibition appears to be cytostatic rather than cytotoxic, and therefore, tumor growth inhibition, or treatment of other angiogenesis dependent diseases, will require prolonged maintenance therapy with the anti-angiogenic agent. It is expected that much of this administration will occur not only in a hospital or medical center but in a home setting. It is extremely important when a drug is administered over extended periods of time by a patient that the mode of administration be relatively simple. In such situations, oral administration is the most preferred mode.

However, formulating such drugs for oral administration has not proven to be a simple process. Frequently, the pharmaceutically active compound is degraded by the acidic and enzymatic conditions of the digestive system. Thus, the ability to administer by an oral route in a stable pharmaceutical form is an extremely important objective.

Heretofore, because of the instability of fumagillol derivatives, they have typically been administered intraveneously. We have now discovered specific pharmaceutical compositions that permit effective oral administration of these important compounds. cl SUMMARY OF THE INVENTION The main object of the present invention is to provide a clinically useful oral dosage form of fumagillol derivatives having angiogenesis inhibitory activity in which the active substance is stable against gastric acid.

Thus, the present invention relates to:

(1) A pharmaceutical composition for oral administration comprising a fumagillol derivative, which composition is stable against gastric acid;

(2) The composition according to (1) which comprises an oleaginous base;

(3) The composition according to (1) which is coated with enteric materials;

(4) The composition according to (2) wherein the fumagillol derivative is dissolved or dispersed in the oleaginous base;

(5) The composition according to (2), wherein the oleaginous base is liquid at room temperature and the proportion of the fumagillol derivative is about 0.001% to about 50% (w/v) relative to the oleaginous base;

(6) The composition according to (2), wherein the oleaginous base is solid at room temperature and the proportion of the fumagillol derivative is about 0.01% to about 100% (w/w) relative to the oleaginous base;

(7) The composition according to (2) wherein the oleaginous base is a fatty acid alcohol ester;

(8) The composition according to (6) wherein the fatty acid alcohol ester is a fatty acid ester of glycerin or polyglycerin;

(9) The composition according to (8) wherein the fatty acid ester of glycerin is a fatty acid triglyceride;

(10) The composition according to (9) wherein the fatty acid triglyceride is a triglyceride of saturated $C_{6-22}$ fatty acid;

(11) The composition according to (2) which is a fine particle having a particle diameter of about 0.1 μm to about 10 mm;

(12) A pharmaceutical composition for oral administration which is produced by drying a suspension comprising a fumagillol derivative, an oleaginous base, and an emulsifier;

(13) The composition according to (1) further comprising a gastric acid antisecretory agent or/and an antacid;

(14) The composition according to (1) wherein the fumagillol derivative is a compound of the formula:

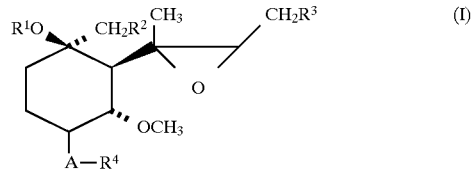

wherein $R^1$ represents hydrogen, $R^2$ represents halogen, $N(O)_m R^5 R^6$, $N^+ R^5 R^6 R^7 . X^-$, $S(O)_n R^5$, or $S^+ R^5 R^6 . X^-$ (where $R^5$, $R^6$ and $R^7$ respectively represent an optionally substituted hydrocarbon group or heterocyclic group, $X^-$ represents a counter anion, m represents an integer of 0 or 1; n represents an integer of 0–2; $R^5$ and $R^6$ may taken together with the adjacent nitrogen or sulfur atom to form an optionally condensed nitrogen- or sulfur-containing heterocyclic group which may substituted), or $R^1$ and $R^2$ together represent a chemical bond; $R^3$ represents an optionally substituted 2-methyl-1-propenyl or isobutyl group; A represents O or $NR^8$ ($R^8$ represents hydrogen, an optionally substituted lower alkyl group, or an optionally substituted aryl group);

3

R$^4$ represents hydrogen, an optionally substituted hydrocarbon group, or an optionally substituted acyl group; or a salt thereof;

(15) The composition according to (14) wherein R$^1$ and R$^2$ together represent a chemical bond or R$^1$ represents hydrogen with R$^2$ representing N(O)$_m$R$^5$R$^6$, N$^+$R$^5$R$^6$R$^7$.X$^-$, S(O)$_n$R$^5$, or S$^+$R$^5$R$^6$.X$^-$ (where each symbol has the same meaning defined in claim 14); A represents O or NH; R$^3$ represents an optionally substituted 2-methyl-1-propenyl or isobutyl group; and R$^4$ represents hydrogen or an optionally substituted carbamoyl group;

(16) The composition according to (15) wherein R$^1$ and R$^2$ together represent a chemical bond;

(17) The composition according to (14) wherein A represents O; R$^3$ represents a 2-methyl-1-propenyl or isobutyl group that may be substituted by hydroxy or dialkylamino; and R$^4$ represents carbamoyl substituted by C$_{1-6}$ alkyl or halo-C$_{1-6}$ alkanoyl;

(18) The composition according to (1) wherein the fumagillol derivative is 6-O-(N-chloroacetylcarbamoyl)-fumagillol;

(19) The composition according to (1) wherein the fumagillol derivative is 4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride;

(20) The composition according to (1) which comprises 6-O-(N-chloroacetylcarbamoyl)fumagillol or a salt thereof and a triglyceride of saturated C$_{6-22}$ fatty acid;

(21) The composition according to (20) comprising about 5 to about 30% (w/v) of 6-O-(N-chloroacetylcarbamoyl)-fumagillol or a salt thereof relative to a triglyceride of saturated C$_{6-22}$ fatty acid;

(22) The composition of (12) which is produced by drying a suspension comprising 6-O-(N-chloroacetylcarbamoyl)fumagillol or a salt thereof, a triglyceride of saturated C$_{6-22}$ fatty acid, and an emulsifier;

(23) The composition according to (1) or (12) which is an angiogenesis inhibitor;

(24) The composition according to (1) or (12) which is an antitumor agent;

(25) An enteric-coated preperation for oral administration comprising a fumagillol derivative;

(26) The preparation of (25) further comprising an oleaginous base;

(27) The preparation of (25) which is a capsule;

(28) A method for treating or preventing angiogenesis-associated diseases which comprises orally administering a fumagillol derivative and a gastric acid secretion-inhibitor or an antacid to a patient in need thereof;

(29) The method of (28), wherein the fumagillol derivative is administered after the administration of the gastric acid secretion/inhibitor and/or the antacid;

(30) A method for treating or preventing angiogenesis-associated diseases which comprises administering the composition of (1) to a patient in need thereof;

(31) A method for treating or preventing angiogenesis associated diseases which comprises administering a fumagillol derivative in combination with a gastric acid secretion-inhibitor and/or an antacid to a patient in need thereof;

(32) A method for treating or preventing angiogenesis associated disease which comprises administering an enteric-coated preparation of (25) to a patient in need thereof.

4

DETAIL DESCRIPTION OF THE INVENTION

Example of the fumagillol derivative used in the present invention includes a fumagillol derivative of the formula:

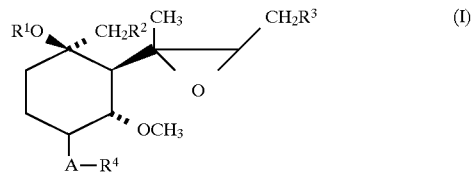

wherein R$^1$ represents hydrogen, R$^2$ represents halogen, N(O)$_m$R$^5$R$^6$, N$^+$R$^5$R$^6$R$^7$.X$^-$, S(O)$_n$R$^5$, or S$^+$R$^5$R$^6$.X$^-$ (where R$^5$, R$^6$ and R$^7$ respectively represent an optionally substituted hydrocarbon group or heterocyclic group, X$^-$ represents a counter anion, m represents an integer of 0 or 1; n represents an integer of 0–2; R$^5$ and R$^6$ may be taken together with the adjacent nitrogen or sulfur atom to form an optionally condensed nitrogen- or sulfur-containing heterocyclic group which may be substituted), or R$^1$ and R$^2$ together represent a chemical bond; R$^3$ represents an optionally substituted 2-methyl-1-propenyl or isobutyl group; A represents O or NR$^8$ (R$^8$ represents hydrogen, an optionally substituted lower alkyl group, or an optionally substituted aryl group); R$^4$ represents hydrogen, an optionally substituted hydrocarbon group, or an optionally substituted acyl group; or a salt thereof.

In the above formula (I), the halogen represented by R$^2$ may for example be fluorine, chlorine, bromine, or iodine. When R$^1$ and R$^2$ represent a chemical bond, an epoxy ring is formed.

The hydrocarbon group of the optionally substituted hydrocarbon group represented by R$^5$, R$^6$, or R$^7$, includes straight-chain or branched C$_{1-6}$ alkyl groups (e.g. methyl, ethyl, propyl, isopropyl, butyl, isobutyl, sec-butyl, pentyl, isopentyl, hexyl, etc.), C$_{2-6}$ alkenyl groups (e.g. vinyl, allyl, 2-butenyl, methylallyl, 3-butenyl, 2-pentenyl, 4-pentenyl, 5-hexenyl, etc.), C$_{2-6}$ alkinyl groups (e.g. ethinyl, propargyl, 2-butin-1-yl, 3-butin-2-yl, 1-pentin-3-yl, 3-pentin-1-yl, 4-pentin-2-yl, 3-hexin-1-yl, etc.), C$_{3-6}$ cycloalkyl groups (e.g. cyclopropyl, cyclobutyl, cyclopentyl, cyclohexyl, etc.), C$_{3-6}$ cycloalkenyl groups (e.g. cyclobutenyl, cyclopentenyl, cyclohexenyl, cyclohexadienyl, etc.), C$_{7-13}$ aralkyl groups (e.g. benzyl, 1-phenethyl, 2-phenethyl, etc.), and C$_{6-10}$ aryl groups (e.g. phenyl, naphthyl, etc.).

The heterocyclic group of the optionally substituted heterocyclic group represented by R$^5$, R$^6$, or R$^7$ includes 5- or 6-membered heterocyclic groups containing 1 to 4 heteroatoms (e.g. nitrogen, oxygen, sulfur, etc.), such as 2-furyl, 2-thienyl, 4-thiazolyl, 4-imidazolyl, 4-pyridyl, 1,3,4-thiadiazol-2-yl, and tetrazolyl. This heterocyclic group may be condensed with a 5- or 6-membered ring which may contain 1 to 3 hetero-atoms (e.g. nitrogen, oxygen, sulfur) other than carbon (e.g. benzene, pyridine, cyclohexane, etc.) to form a condensed bicyclic group (e.g. 8-quinolyl, 8-purinyl, etc.).

The nitrogen-containing heterocyclic group which may be formed by R$^5$ and R$^6$ together with the adjacent nitrogen atom includes 4- to 7-membered nitrogen-containing heterocyclic groups which may contain 1 to 3 hetero-atoms (e.g. nitrogen, oxygen, sulfur) other than a nitrogen atom (e.g. pyrrolidin-1-yl, piperidino, morpholino, piperazin-1-yl, etc.).

The sulfur-containing heterocyclic group which may be formed by R$^5$ and R$^6$ together with the adjacent sulfur atom includes 4- to 7-membered sulfur-containing heterocyclic groups which may contain 1 to 3 hetero-atoms (e.g. nitrogen, oxygen, sulfur) other than a sulfur atom (e.g. tetrahydrothiophen-1-yl, 1,4-thioxan-1-yl, etc.).

The nitrogen- or sulfur-containing heterocyclic group which may be formed by $R^5$ and $R^6$ together with the adjacent nitrogen or sulfur atom may be condensed to a 5- or 6-membered ring (e.g. benzene, pyridine, pyrazine, pyrimidine, pyridazine, cyclohexane, etc.) to form a condensed bicyclic group (e.g. isoindolin-2-yl, 2-isoquinolyl, 1,3-dihydrobenzo[c]thiophen-2-yl, 2,3-dihydrobenzo[b] thiophen-l-yl, 3,4-dihydro-1H-2-benzopyran-2-yl, 3,4-dihydro-2H-1-benzopyran-1-yl, 1,2,4,5-tetrahydro-3-benzothiepin-3-yl, 1,3-dihydrothieno[3,4-c]pyridin-2-yl, 5,7-dihydrothieno[3,4-b]-pyrazin-6-yl, 5,7-dihydrothieno[3,4-d]pyridazin-6-yl, etc.).

The lower alkyl group of the optionally substituted lower alkyl group represented by $R^8$ includes straight-chain or branched $C_{1-6}$ alkyl groups (e.g. methyl, ethyl, propyl, isopropyl, butyl, isobutyl, sec-butyl, pentyl, isopentyl, hexyl, etc.).

The aryl group of optionally substituted aryl group represented by $R^8$ includes $C_{6-10}$ aryl groups (e.g. phenyl, naphthyl, etc.).

The optionally substituted hydrocarbon group represented by for $R^4$ includes those described with respect to that of the optionally substituted hydrocarbon group $R^6$ or $R^7$.

When the hydrocarbon group represented by $R^4$ is an alkenyl group, it is preferably unsubstituted.

The optionally substituted acyl group mentioned represented by $R^4$ includes residues of acid (acyl group derived from corresponding acids) such as carboxylic acid-acyl, such sulfonic acid-acyl, carbamoyl, thiocarbamoyl and sulfamoyl each of which may have a substituent. More specifically, alkanoyl, aroyl, heterocycle-carbonyl, carbamoyl, thiocarbamoyl, arylsulfonyl, alkylsulfonyl, sulfamoyl, alkoxycarbonyl, and aryloxycarbonyl, each of which may have a substituent. Optionally substituted carbamoyl is preferable.

The alkanoyl group of optionally substituted alkanoyl group includes $C_{1-6}$ alkanoyl groups (e.g. formyl, acetyl, propionyl, isopropionyl, butyryl, pentanoyl, hexanoyl, etc.).

The aroyl group of the optionally substituted aroyl group includes $C_{7-11}$ aroyl groups (e.g. benzoyl, 1-naphthoyl, 2-naphthoyl, etc.).

The heterocycle-carbonyl group of the optionally substituted heterocycle-carbonyl group includes 5- or 6-membered heterocyclic carbonyl groups containing 1 to 4 hetero-atoms (e.g. nitrogen, oxygen, sulfur, etc.), such as 2-furoyl, 2-thenoyl, nicotinoyl, and isonicotinoyl.

The particular arylsulfonyl group of the optionally substituted arylsulfonyl group includes $C_{6-10}$ arylsulfonyl groups (e.g. benzenesulfonyl, 1-naphthylsulfonyl, 2-naphthylsulfonyl, etc.).

The particular alkylsulfonyl group of the optionally substituted alkylsulfonyl group includes $C_{1-6}$ alkylsulfonyl groups (e.g. methylsulfonyl, ethylsulfonyl, propylsulfonyl, butylsulfonyl, pentylsulfonyl, etc.).

The alkoxycarbonyl group of the optionally substituted alkoxycarbonyl group includes $C_{2-7}$ alkoxycarbonyl groups (e.g. methoxycarbonyl, ethoxycarbonyl, isobutoxycarbonyl, etc.)

The particular aryloxycarbonyl group of the optionally substituted aryloxycarbonyl group includes $C_{7-11}$ aryloxycarbonyl groups (e.g. phenoxycarbonyl, 1-naphthyloxycarbonyl, 2-naphthyloxycarbonyl, etc.).

The substituent group on the optionally substituted 2-methyl-1-propenyl or isobutyl group represented by $R^3$ includes hydroxy, amino, lower($C_{1-3}$) alkylamino (e.g. methylamino, ethylamino, isopropyl-amino, etc.), and di-lower($C_{1-3}$) alkylamino group (e.g. dimethylamino, diethylamino, etc.). Among those substituent groups, hydroxy and di-lower($C_{1-3}$) alkylamino and particularly dimethylamino, are preferred.

The optionally substituted hydrocarbon or heterocyclic group represented by $R^5$, $R^6$, or $R^7$, the optionally condensed nitrogen- or sulfur-containing heterocyclic group formed by $R^5$ and $R^6$ together with the adjacent nitrogen or sulfur atom, the optionally substituted lower alkyl or aryl group represented by $R^8$, and the optionally substituted hydrocarbon or acyl group (e.g. alkanoyl, aroyl, heterocyclic carbonyl, carbamoyl, thiocarbamoyl, arylsulfonyl, alkylsulfonyl, sulfamoyl, alkoxycarbonyl, aryloxycarbonyl) represented by $R^4$ may have 1 to 3 substituents at the possible positions.

Examples of such substituents include $C_{1-6}$ alkyl groups (e.g. methyl, ethyl, propyl, isopropyl, butyl, isobutyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkynyl groups (e.g. ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl groups (e.g. cyclopropyl, cyclobutyl, cyclopentyl, cyclohexyl, etc.), $C_{3-6}$ cycloalkenyl groups (e.g. cyclobutenyl, cyclopentenyl, cyclohexenyl, cyclohexadienyl, etc.), $C_{6-10}$ aryl groups (e.g. phenyl, naphthyl, etc.), amino group, mono-$C_{1-6}$ alkylamino groups (e.g. methylamino, ethylamino, isopropylamino, etc.), di-$C_{1-6}$ alkylamino groups (e.g. dimethylamino, diethylamino, etc.), azido group, nitro group, halogen (e.g. fluorine, chlorine, bromine, iodine), hydroxy group, $C_{1-4}$ alkoxy groups (e.g. methoxy, ethoxy, etc.), $C_{6-10}$ aryloxy groups (e.g. phenoxy, naphthyloxy, etc.), $C_{1-6}$ alkylthio groups (e.g. methylthio, ethylthio, propylthio, etc.), $C_{6-10}$ arylthio groups (e.g. phenylthio, naphthylthio, etc.), cyano group, carbamoyl group, carboxy group, $C_{1-4}$ alkoxycarbonyl groups (e.g. methoxycarbonyl, ethoxycarbonyl, etc.), $C_{7-11}$ aryloxycarbonyl groups (e.g. phenoxycarbonyl, 1-naphthyloxycarbonyl, 2-naphthyloxycarbonyl, etc.), carboxy-$C_{1-4}$ alkoxy groups (e.g. carboxymethoxy, 2-carboxyethoxy, etc.), $C_{1-6}$ alkanoyl groups (e.g. formyl, acetyl, propionyl, isopropionyl, butyryl, pentanoyl, hexanoyl, etc.), $C_{7-11}$ aroyl groups (e.g. benzoyl, 1-naphthoyl, 2-naphthoyl, etc.), $C_{1-6}$ alkylsulfonyl groups (e.g. methylsulfonyl, ethylsulfonyl, etc.), $C_{6-10}$ arylsulfonyl groups (e.g. benzenesulfonyl, 1-naphthylsulfonyl, 2-naphthylsulfonyl, etc.), $C_{1-6}$ alkylsulfinyl groups (e.g methylsulfinyl, ethylsulfinyl, etc.), $C_{6-10}$ arylsulfinyl groups (e.g. benzenesulfinyl, 1-naphthylsulfinyl, 2-naphthylsulfinyl, etc.), 5- or 6-membered heterocyclic groups containing 1 to 4 hetero-atoms (e.g. nitrogen, oxygen, sulfur) (e.g. 2-furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl groups containing 1 to 4 hetero-atoms (e.g. nitrogen, oxygen, sulfur) (e.g. 2-furoyl, 2-thenoyl, nicotinoyl, isonicotinoyl, etc.), and 5- or 6-membered heterocyclic thio groups containing 1 to 4 hetero-atoms (e.g. nitrogen, oxygen, sulfur) (e.g. 4-pyridylthio, 2-pyrimidylthio, 1,3,4-thiadiazol-2-ylthio, 1-methyl-5-tetrazolylthio, etc.). Further, the heterocyclic thio groups may be condensed with a benzene ring to form a condensed bicyclic thio group (e.g. 2-benzothiazolylthio, 8-quinolylthio, etc.). Among those substituents, $C_{1-6}$ alkyl groups and $C_{1-6}$ alkanoyl groups are preferred. Furthermore, when $R^4$ represents a di-substituted carbamoyl, thiocarbamoyl, or sulfamoyl group, the carbamoyl, thiocarbamoyl, or sulfamoyl group together with the nitrogen atom thereof may form a nitrogen-containing heterocyclic group such as 4- to 7-membered nitrogen-containing heterocyclic groups which may contain 1 to 3 hetero-atoms (e.g. nitrogen, oxygen, sulfur) other than the nitrogen atom, such as pyrrolidin-1-yl, piperidino, morpholino, piperazin-1-yl, 4-methylpiperazin-1-yl and 4-phenylpiperazin-1-yl.

The substituent in the optionally substituted hydrocarbon or heterocyclic group represented by $R^5$, $R^6$ or $R^7$; the substituent in the optionally condensed nitrogen- or sulfur-containing heterocyclic group that may be formed by $R^5$ and $R^6$ together with the adjacent nitrogen or sulfur atom; the substituent in the optionally substituted lower alkyl or aryl group represented by $R^8$, and the substituent in the optionally substituted hydrocarbon or acyl group represented by $R^4$ (e.g. alkanoyl, aroyl, heterocyclic carbonyl, carbamoyl, thiocarbamoyl, arylsulfonyl, alkylsulfonyl, sulfamoyl, alkoxycarbonyl, or aryloxycarbonyl) may further contain 1 to 3 substituents at the possible positions.

Examples of such substituent include the aforementioned $C_{1-6}$ alkyl groups, $C_{2-6}$ alkenyl groups, $C_{2-6}$ alkynyl groups, $C_{3-6}$ cycloalkyl groups, $C_{3-6}$ cycloalkenyl groups, $C_{6-10}$ aryl groups, amino group, mono-$C_{1-6}$ alkylamino groups, di-$C_{1-6}$ alkylamino groups, azido group, nitro group, halogen group, hydroxy group, $C_{1-4}$ alkoxy groups, $C_{6-10}$ aryloxy groups, $C_{1-6}$ alkylthio groups, $C_{6-10}$ arylthio groups, cyano group, carbamoyl group, carboxy group, $C_{1-4}$ alkoxy-carbonyl groups, $C_{7-11}$ aryloxycarbonyl groups, carboxy-$C_{1-4}$ alkoxy groups, $C_{1-6}$ alkanoyl groups, halo-$C_{1-6}$ alkanoyl groups, $C_{7-11}$ aroyl groups, $C_{1-6}$ alkylsulfonyl groups, $C_{6-10}$ arylsulfonyl groups, $C_{1-6}$ alkylsulfinyl groups, $C_{6-10}$ arylsulfinyl groups, 5- or 6-membered heterocyclic groups, 5- or 6-membered heterocyclic carbonyl groups, and 5- or 6-membered heterocyclic thio groups.

The counter anion represented by $X^-$ includes halogen ion (e.g. iodide ion, bromide ion, chloride ion), sulfate ion, phosphate ion, nitrate ion, perchlorate ion, tetrafluoroborate ion, methanesulfonate ion, p-tolylsulfate ion, benzenesulfate ion, hydroxyl ion, and organic carboxylate ions (e.g. oxalate ion, maleate ion, fumarate ion, succinate ion, citrate ion, lactate ion, trifluoroacetate ion, lactobionate ion, acetate ion, propionate ion, tartrate ion, ethylsuccinate ion, etc.). Preferred are halide ions.

The compound of the formula (I) above (hereinafter sometimes referred to as compound (I)) has symmetric centers in its molecule and is optically active. However, its absolute configuration is based on the starting material, fumagillol and the absolute configuration is consistent with that of the fumagillol unless otherwise specified. The modes of bonding of the substients on the cyclohexane ring are as follows;

The symbol . . . represents α-bond,

◄ represents β-bond, and

—— represents an option of α- and β-bond.

In the compound (I), preferably $R^1$ and $R^2$ together represent a chemical bond, or $R^1$ represents hydrogen and $R^2$ represents $N(O)_m R^5 R^6$, $N^+ R^5 R^6 R^7 . X^-$, $S(O)_n R^5$, or $S^+ R^5 R^6 . X^-$, more preferably $S^+ R^5 R^6 . X^-$ respectively. It is also preferable that the sulfur-containing heterocyclic group formed by $R^5$ and $R^6$ together with the adjacent sulfur atom, which may be condensed with a 5- or 6-membered ring to form a condensed bicyclic group. In compound (I), $R^1$ and $R^2$ together represent a chemical bond is more preferred.

A is preferably O or NH, and more preferably O.

$R^3$ is preferably a 2-methyl-1-propenyl or isobutyl group, which may be substituted by hydroxy or dialkylamino group. Particularly more preferred is 2-methyl-1-propenyl.

$R^4$ is preferably hydrogen or an optionally substituted carbamoyl group. Particularly preferred is carbamoyl substituted by $C_{1-6}$ alkyl group or $C_{1-6}$ alkanoyl group may be substituted by halogen.

Preferred examples of the compound (I) include 6-O-(N-chloroacetylcarbamoyl)fumagillol, 6α-(N'-chloroacetylureido)-6-desoxyfumagillol, 4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride, and 6-O-(N-methylcarbamoyl)fumagillol.

When compound (I) has an acidic substituent (e.g. carboxy) or a basic substituent (e.g. amino, mono-lower alkylamino, di-lower alkylamino, or a nitrogen-containing heterocyclic group) in the molecule, it may form a physiologically acceptable salt. Examples of the physiologically acceptable salt include salts with inorganic bases, salts with organic bases, salts with inorganic acids, salts with organic acids, and salts with basic or acidic amino acids. The inorganic base capable of forming such a salt includes alkali metals (e.g. sodium, potassium, etc.) and alkaline earth metals (e.g. calcium, magnesium, etc.). Such the organic base includes trimethylamine, triethylamine, pyridine, picoline, N,N-dibenzylethylenediamine, ethanolamine, diethanolamine, tris(hydroxymethyl)amino-methane, and dicyclohexylamine. Such the inorganic acid includes hydrochloric acid, hydrobromic acid, sulfuric acid, nitric acid and phosphoric acid. Such the organic acid includes formic acid, acetic acid, trifluoroacetic acid, oxalic acid, tartaric acid, fumaric acid, maleic acid, methanesulfonic acid, benzene-sulfonic acid and p-toluenesulfonic acid. Such the basic or acidic amino acid includes arginine, lysine, ornithine, aspartic acid, and glutamic acid. Among those salts, the salt with bases (i.e. the salt with inorganic bases, the salt with organic bases, or the salt with basic amino acids) those can be formed with the free carboxyl group in the substituent of the compound (I), and the salts with acid (i.e. the salts with inorganic acids, salt with organic acids, or salt with acidic amino acids) represent those which can be formed with the amino, mono-lower alkylamino, di-lower-alkylamino, or nitrogen-containing heterocyclic groups in the substituent of the compound (I).

In case compound (I) contains a di-lower alkylamino group, a nitrogen-containing heterocyclic group, or a nitrogen-containing aromatic heterocyclic group, the nitrogen atom in such a group may be further alkylated to form a quaternary ammonio group (e.g. trimethylammonio, N-methylpyridinyl, N-methylpyrrolidin-1-ylium, etc.) and the counter anion may be similar to the counter anion shown with respect to $X^-$ mentioned hereinbefore.

Compound (I) and its a salt can be produced using, as a starting material, fumagillol which is a hydrolyzate of fumagillin which is produced by micro-organisms [Tarbell. D. S. et al, J. Am. Chem. Soc., 83, 3096, (1961)] in accordance with the process described in the aforementioned EP official gazettes (e.g. EP-A-357,061 etc.) or a method analogous thereto. The physicochemical and biological properties of the compound are also described in detail in the EP official gazettes described hereinbefore.

In the pharmaceutical composition for oral administration and the preparation thereof comprising a fumagillol derivative of the present invention, the derivative is stabilized against gastric acid by at least one of the following means in order to protect the fumagillol derivative.

(1) Compounding an oleaginous base into the composition:
(2) Enteric coating the composition:
(3) Comprising a gastric acid secretion-inhibitor or/and an antacid:

The oleaginous base used in the present invention, preferably includes fatty acid alcohol esters, oils and hydrogenated oils, waxes, saturated higher fatty acids, higher alcohols, phospholipids, and hydrocarbons in view of stabilizing the fumagillol derivative and a property of oral absorption thereof. Particularly, fatty acid alcohol esters can be employed extensively.

The fatty acids of the fatty acid alcohol esteres may be either monocarboxylic acid or dicarboxylic acids. Specifically, the dicarboxylic acid includes such as oxalic acid, malonic acid, succinic acid, glutaric acid, adipic acid, maleic acid, fumaric acid, phthalic acid, isophthalic acid, terephthalic acid, and sebacic acid. The monocarboxylic acid includes $C_6$–$C_{22}$ aliphatic carboxylic acids, e.g. caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), arachidic acid ($C_{20}$), behenic acid ($C_{22}$), particularly medium-chain ($C_{6-14}$) fatty acids is preferable.

The alcohols of the fatty acid alcohol esteres include $C_{1-20}$ alcohols such as methyl alcohol, ethyl alcohol, n-propyl alcohol, n-butyl alcohol, n-pentyl alcohol, n-hexyl alcohol, n-heptyl alcohol, n-octyl alcohol, n-decyl alcohol, n-lauryl alcohol, n-myristyl alcohol, n-cetyl alcohol, n-octadecyl alcohol, isopropyl alcohol, isobutyl alcohol, sec-butyl alcohol, tert-butyl alcohol, isopentyl alcohol, tert-pentyl alcohol; ethylene glycol, propylene glycol, 1,3-propanediol; and glycerin. Polymerized polyhydric alcohols such as polyglycerin are also exemplified.

The fatty acid alcohol ester may be any ester prepared by the above-mentioned fatty acids and alcohols as long as it can be used for pharmaceutical preparation. When polyhydric alcohol is used, the fatty acid to be esterificated may be same or different.

Fatty acid esters of glycerin or polyglycerin are preferable among others. The ratio of esterified hydroxyl groups relative to the total hydroxyl groups (degree of esterification) in the fatty acid ester of glycerin or polyglycerin is preferably not less than about 60%, more preferably not less than about 80%. The degree of polymerization of the polyglycerin is preferably 2 to 16.

Those fatty acid esters of glycerin or polyglycerin are used alone or in combination with two or more thereof. Preferably, the fatty acid esters are appropriately selected so that degree of esterification becomes not less than about 60%, more preferably not less than about 80%.

The fatty acids ester of glycerin are preferably fatty acid triglycerides (triacylglycerin) wherein 3 molecules of the fatty acid are attached to one molecule of glycerin through ester linkage. The fatty acid to be esterificated may be the same or different and are preferably saturated fatty acids having 6 to 22 carbon atoms. Saturated fatty acids having 8 to 18 carbon atoms are more preferred. Particularly, those of 8 to 12 carbon atoms are most preferred.

The fatty acid ester of glycerin include the commercially available products such as Miglyol 810 (caprylic/capric acid triglyceride; fatty acid composition: 65–75% caprylic acid and 25–35% capric acid), Miglyol 812 (caprylic/capric acid triglyceride; fatty acid composition: 50–65% caprylic acid and 30–45% capric acid), Miglyol 829 (glyceryl succinate di(caprylate/caprate); fatty acid composition: 35–45% caprylic acid, 20–30% capric acid, 12–16% succinic acid), Miglyol 840 (propylene glycol dicaprylate; fatty acid composition: 65–80% caprylic acid and 15–30% capric acid), Dynasan 110 (capric acid triglyceride), Dynasan 112 (lauric acid triglyceride), Dinasan 114 (myristic acid triglyceride), Dynasan 116 (palmitic acid triglyceride) and Dynasan 118 (stearic acid triglyceride) available from Huls Aktiengesellschaft, Germany; and Triester-F-810 (caprylic/capric acid triglyceride) is available from Nikko Chemicals Co., Tokyo. These glycerides can be used as a mixture of two or more of them.

The fatty acid esters of polyglycerins are preferably those wherein the polyglycerins are selected from various glycerin polymers whose degree of polymerization of glycerin is 2–16 particularly preferably 2–10. At least one, preferably not less than about 60%, more preferably not less than 80%, of the total hydroxyl groups (the degree of polymerization+ 2) is attached to fatty acid through ester linkage. The fatty acid is preferably a saturated fatty acid, particularly a saturated fatty acid having 6–22, more preferably 8–18 carbon atoms. The fatty acid to be esterified may be the same or different. Various polyglycerin fatty acid esters varying in the degree of polymerization of glycerin, the kind of fatty acid, and the degree of esterification are commercially available and any of them can be employed in the present invention.

The fatty acid ester of polyglycerins are also commercially available. For example, PS-310 (tetraglycerin pentastearate), MS-310 (tetraglycerin monostearate), HB-310 (tetraglycerin hexabehenate), PO-310 (tetraglycerin pentaoleate), PO-500 (hexaglycerin monostearate), DAO-750 (decaglycerin decaoleate), DAS-750 (decaglycerin decastearate), etc. are available from Sakamoto Yakuhin Kogyo, Co. Ltd. (Osaka); Poem J46B (tetraglycerin hexabehenate), are available from Riken Vitamin Co. (Tokyo); and Tetraglyn 5-S (tetraglycerin pentastearate), Decaglyn 10-S (decaglycerin decastearate), etc. are available from Nikko Chemicals (Tokyo).

These polyglycerin esters can be used alone or as a mixture of two or more of them. It is also possible to use them in combination with other oleaginous bases such as glycerin fatty acid esters.

The oils and fatty oils include such as soybean oil, olive oil, rape seed oil, peppermint oil, sesame oil, castor oil, camellia oil, wheat germ oil, fennel oil, corn oil, sunflower oil, cotton seed oil, coconut oil and peanut oil, and the corresponding hydrogenated oils.

The waxes include carnauba wax, spermaceti, etc.

The saturated fatty acids include $C_8$–$C_{22}$ fatty acids, such as caprylic acid, capric acid, palmitic acid, stearic acid and behenic acid, and salts thereof.

The higher alcohols includes $C_{10}$–$C_{20}$ alcohols such as cetyl alcohol, and stearyl alcohol.

The phospholipids include, for example, hydrogenated lecithin.

The hydrocarbons include such as paraffin and microcrystalline wax.

The above-mentioned oleaginous bases can be used alone or in combination with two or more of them.

From the viewpoint of the stabilizing effect and the efficiency of oral absorption of the fumagillol derivative, a fatty acid ester of glycerin or a polyglycerin is extensively used as the oleaginous base.

The pharmaceutical composition of the present invention can be used for an oral dosage form of a fumagillol derivative wherein the derivative is stabilized against gastric acid. This pharmaceutical composition may be in liquid form or solid form. The pharmaceutical composition can be prepared by the per se known method. For example, the following methods can be employed.

When an oleaginous base which is liquid at room temperature (5°–30° C.) is employed, the fumagillol derivative is added to the base and dissolved or dispersed in it by a method such as agitation to provide the composition.

When an oleaginous base which is solid at room temperature (5°–30° C.) is employed, it is converted into a liquid form and the fumagillol derivative is then dissolved or dispersed therein, followed by solidification. In the per se known manner, the oleaginous base is warmed at least to its melting point and the fumagillol derivative is dissolved or dispersed in a liquid form thereof, followed by cooling for solidification. Solidification may be carried out, if necessary, so as to form particles or pelletes. This formation can be carried out by the per se known method. In the case of forming particles, for example, spherical microparticles having particle diameters of about 0.1 μm to about 1000 μm. This formation can be achieved by the per se known method (e.g. JP-A-223533/1991). Examples of the method includes the method in which a solution or dispersion of the fumagillol derivative is dispersed into an aqueous phase, the spray drying method, and the spray chilling method which comprises preparing fine oil droplets and solidifying them by rapid chilling. As the "aqueous phase", an aqueous medium optionally containing a dispersant (e.g. Tween 80, carboxymethylcellulose, polyvinyl alcohol, etc.) can be employed for avoiding aggregation of the particles.

The proportion of the fumagillol derivative relative to the oleaginous base in the composition can be appropriately selected according to the physicochemical properties such as solubility, dispersibility and the effective dose of the fumagillol derivative. When the oleaginous base is a liquid, the proportion is preferably about 0.001 to about 50% (w/v) and more preferably about 5 to about 30% (w/v) relative to the liquid oleaginous base. When the oleaginous base is a solid, the proportion of the fumagillol derivative is about 0.01 to about 900% (w/w) and more preferably about 0.01 to about 100% (w/w) relative to the solid oleaginous base.

The concentration or content of the fumagillol derivative in the composition can be appropriately selected according to the physicochemical properties of the composition. When the composition is in a liquid form, the concentration is about 0.0005 to about 30% (w/v) and preferably about 0.005 to about 25% (w/v). When the composition is a solid, the content is about 0.01 to about 90% (w/w) and preferably about 0.1 to about 50% (w/w).

If necessary, additives such as a preservative (e.g. benzyl alcohol, ethyl alcohol, benzalkonium chloride, phenol, chlorobutanol, etc.), an antioxidant (e.g. butylhydroxyanisole, propyl gallate, ascorbyl palmitate, α-tocopherol, etc.), and a thickener (e.g. lecithin, hydroxypropylcellulose, aluminum stearate, etc.) can be used.

The suspension of the present invention comprising the fumagillol derivative, oleaginous base and emulsifier, which is generally referred to as lipid microspheres or lipid nanospheres, and the composition available upon drying this suspension, which is generally known as a dry emulsion, can be prepared by the per se known technology. Thus, the oleaginous base (glycerin fatty acid ester, polyglycerin fatty acid ester, aliphatic alcohol fatty acid ester, vegetable oil, or a mixture of two or more of them) in which the fumagillol derivative has been dissolved or dispersed is emulsified in an aqueous medium with the aid of an emulsifier to provide the desired composition in a form of fine droplets having a mean particle diameter of about 10 to about 500 nm.

As the emulsifier for use in the present invention, any pharmaceutically acceptable emulsifier can be employed. Particularly preferred are pharmaceutically acceptable phospholipids and nonionic surfactants. The emulsifiers can be used alone or in combination with two or more of them. The phospholipid includes naturally occurring phospholipids, e.g. egg yolk lecithin, soya lecithin, and their hydrogenation products, and synthetic phospholipids, e.g. phosphatidylcholine, phosphatidylethanolamine, etc. Among them, egg yolk lecithin, soya lecithin, and phosphatidylcholine derived from egg yolk or soybean are preferred. The nonionic surfactant includes macro-molecular surfactants with molecular weights in the range of about 800 to about 20,000, such as polyethylene-propylene copolymer, polyoxyethylene alkyl ethers, polyoxyethylene alkylarylethers, hydrogenated castor oil-polyoxyethylene derivatives, polyoxyethylene sorbitan derivatives, polyoxyethylene sorbitol derivatives, polyoxyethylene alkyl ether sulfate, and so on. The proportion of the emulsifier is selected so that the concentration in an final administrable composition will be in the range of about 0.1 to about 10%, preferably about 0.5 to about 5%.

In addition to the above-mentioned components, a stabilizer for further improving the stability of the active substance, such as an antioxidant or a chelating agent, an isotonizing agent for adjusting the osmolarity, an auxiliary emulsifier for improving the emulsifying power, and/or an emulsion stabilizer for improving the stability of the emulsifying agent can be incorporated.

The isotonizing agent that can be used includes, for example, gylcerin, sugar alcohols, monosaccharides, disaccharides, amino acids, dextran, albumin, etc. These isotonizing agents can be used each alone or in combination with two or more of them.

The stabilizer for the active substance includes antioxidants, e.g. ascorbic acid, tocopherol, sorbic acid, retinol, etc.; and the chelating agents such as citric acid, tartaric acid, etc. The proportion of the stabilizer is selected so that its concentration in the final administrable composition will be about 0.00001 to about 10%, preferably about 0.0001 to about 5%.

Examples of the auxiliary emulsifier include fatty acids having 6–30 carbon atoms and their salts or monoglycerides, e.g. caproic acid, capric acid, caprylic acid, lauric acid, myristic acid, palmitic acid, stearic acid, behenic acid, palmitoleic acid, oleic acid, linoleic acid, arachidonic acid, eicosapentanoic acid, docosahexenic acid, etc., the carboxylic acid salts of them, such as the salts with sodium, potassium, calcium, etc., and the monoglycerides of carboxylic group thereof.

The emulsion stabilizer that can be used includes cholesterol, cholesterol esters, tocopherol, albumin, fatty acid amide derivatives, polysaccharides, polysaccharide fatty acid ester derivatives, etc.

The pharmaceutical composition of the present invention may comprise a viscogenic substance which can adhere to the digestive tract mucosa due to its viscosity expressed on exposure to water. The examples of the viscogenic substance include, but are not particularly limited as long as it is pharmaceutically acceptable, such as polymers (e.g. polymers or copolymers of acrylic acids and their salts) and natural-occuring viscogenic substances (e.g. mucins, agar, gelatin, pectin, carrageenin, sodium alginate, locust bean gum, xanthan gum, tragacanth gum, arabic gum, chitosan, pullulan, waxy starch, sucralfate, curdlan, cellulose, and their derivatives). Furthermore, for control the release of the active drug or for formulation purposes, the additives conventionally used for preparing the oral compositions can be added. Example of the additives include excipients (e.g. lactose, corn starch, talc, crystalline cellulose, sugar powder, magnesium stearate, mannitol, light anhydrous silicic acid, magnesium carbonate, calcium carbonate, L-cysteine, etc.), binders (e.g. starch, sucrose, gelatin, arabic gum powder, methylcellulose, carboxymethylcellulose, carboxymethylcellulose sodium, hydroxypropylcellulose, hydroxypropylmethylcellulose, polyvinylpyrrolidone, pullulan, dextrin, etc.), disintegrators (e.g. carboxymethylcellulose calcium, low-substituted hydroxypropylcellulose, croscarmellose sodium, etc.), anionic surfactants (e.g. sodium alkylsulfates etc.), nonionic surfactants (e.g. polyoxyethylene sorbitan fatty acid esters, polyoxyethylene fatty acid esters, polyoxyethylene-castor oil derivatives, etc.), antacids and mucous membrane protectants (e.g. magnesium hydroxide, magnesium oxide, aluminum hydroxide, aluminum sulfate, magnesium metasilicate aluminate, magnesium silicate aluminate, sucralfate, etc.), cyclodextrin and the corresponding carboxylic acid (e.g. maltosyl-β-cyclodextrin, maltosyl-β-cyclodextrin-carboxylic acid, etc.), colorants, corrigents, adsorbents, antiseptics, moistening agents, antistatic agents, disintegration retardants, and so on. The proportion of these additives can be appropriately selected from the range that can keep the stability and absorption of the basis.

The pharmaceutical composition for oral administration of the present invention may also include flavoring agents. Such agents include, for example, anise oil, lavender oil, lemon oil, orange essence, rose oil, powder green tea, bergamot oil, (αl) borneol, Natural Peal Extract AH-10, Sugar, bitter essence, pine flavor etc.

The pharmaceutical composition for oral administration of the present invention can be prepared generally by the known procedure or any procedure analogous thereto. Specifically, in the emulsification procedure, which can carried out according to the known emulsification technology, the drug is preferably dissolved or dispersed in the oil beforehand. The following is a preferred procedure. Thus, the basis, oil base, and emulsifier, optionally together with an isotonizing agent, a stabilizer for the basis, an auxiliary emulsifier, and an emulsion stabilizer, are mixed in a predetermined ratio and is warmed to a temperature of about 30° to about 90° C., preferably about 40° to about 80° C. folowed by addition of a predetermined amount of water and mixing. The mixture is homogenized using a conventional homogenizer or homomixer (e.g. jet homogenizer, ultrasonic homogenizer, high-speed revolving homogenizer, etc.) to prepare a crude emulsion. This crude emulsion is added to water according to the necessity, further homogenized with the above-mentioned homogenizer. The resulting emulsion is filtered to eliminate coarse particles over 5 μm to provide the desired emulsion. The particle diameter is preferably in the range of about 0.01 to about 5 μm (about 10 to about 5,000 nm), more preferably in the range of about 0.01 to about 0.5 μm (about 10 to about 500 nm), and for still better results, in the range of about 0.02 to about 0.2 μm (about 20 to about 200 nm).

For the purpose of preventing association or aggitation of particles in the oil phase during the drying of the suspension, various additives (e.g. sugars such as trehalose, maltose, lactose, sucrose, saccharose, mannitol and glucose, basic amino acids, neutral amino acids, acidic amino acids, sodium chloride, etc.) may be added in the course of preparation of the suspension. Dehydration of the suspension can be carried out typically by vacuum drying, spray drying, or freeze drying and like.

The composition of the present invention is preferably particle and their mean particle diameter is about 0.01 μm to about 10 mm preferably about 0.1 μm to about 10 mm. When the composition is a solid, its particle diameter is preferably about 1 μm to about 10 mm. When it is a liquid, its particle diameter is preferably about 0.1 μm to about 1,000 μm.

The composition of the present invention is preferably stabilized against gastric acid by formulating the active substance with an oleaginous base and/or enteric coating. However, a pharmaceutical composition for oral administration comprising a fumagillol derivative which is not treated with any of these measure for stabilized against gastric acid can also be used in the drug in accordance with the invention. In this case, the composition may be used in admixture or in combination with a gastric acid secretion-inhibitor and/or an antacid.

The gastric acid secretion inhibitor includes such as $H_2$ blockers (e.g. famotidine, cimetidine, ranitidine hydrochloride, etc.) and proton pump inhibitors (e.g. lansoprazole, omeprazole, etc.). As the antacid, compounds which elevate the intragastric pH level, such as magnesium carbonate, sodium hydrogen carbonate, magnesium hydroxide, magnesium oxide and magnesium hydroxide can be employed.

The oral dosage form using the composition of the present invention is preferably administered after the intragastric pH has been increased to alleviate the influence of gastric acid by the administration of the gastric acid secretion inhibitor and/or antacid.

The pharmaceutical composition of the invention may be in a form of enteric-coated preparation for oral administration comprising fumagillol. The drug (fumagillol derivative) containing core for coating an enteric coating film can be prepared by the above-mentioned method with using an oleaginous base or by per se know formulation method without using an oleaginous base.

In the composition of the present invention, the form of the drug-containing core for coating with a coating agent may be, for example, tablets, pills and granules.

The drug containing-core can be prepared by an ordinary production method. For example, when the core is prepared in a granule form, it can be prepared by mixing the drug with an appropriate excipient, binder, disintegrant, lubricant etc., then conducting wet extrusion granulation, fluidized bed granulation, or the like.

The excipient contained in the core is exemplified by saccharides, such as sucrose, lactose, mannitol and glucose, starch, crystalline cellulose and calcium phosphate.

Useful binders include polyvinyl alcohol, hydroxypropyl cellulose, macrogol, Pluronic F-68, gum arabic, gelatin and starch. Useful disintegrants include carboxymethyl cellulose calcium (ECG505), crosslinked carboxymethylcellulose sodium (Ac-Di-Sol), polyvinylpyrrolidone and low-substituted hydroxypropyl cellulose (L-HPC). Useful lubricants and antiflocculants include talc and magnesium stearate.

In addition to the above production method, the drug containing-core can also be prepared by, for example, tumbling granulation, pan coating, fluidized bed coating and melting granulation in which the drug, or its mixture with a excipient, lubricant etc., is added little by little, while a binder, dissolved in an appropriate organic solvent, such as a lower alcohol (e.g., methanol, ethanol), is sprayed over an inert carrier particles for the core center. Useful inert carrier particles include those produced from sucrose, lactose, starch, crystalline cellulose or wax.

The core components may also include the above-mentioned pharmaceutically acceptable additives or excipients.

The content of the fumagillol derivatives in the resulting core may be selected so as to make the content relative to the final composition in the above-mentioned range.

The resulting drug-containing core may be surface coated with a protecting agent before the drug is separated from the enteric-coating film. The protecting agents include hydrophilic substances such as polysaccharide having a sulfate group, hydroxyalkyl group or carboxyalkyl group. As protecting agents, polysaccharides having a hydroxyalkyl group or carboxyalkyl group such as hydroxypropylmethyl cellulose are preferably used. When a protecting agent is used, it can be coated by an ordinary coating method. Specifically, it can be coated by spray coating the core using, for example, fluidized bed coating or pan coating.

The enteric coating agent is an enteric polymer which is substantially insoluble in the acidic pH and is at least partially soluble at weaker acidic pH through the basic pH range. The range of acidic pH is about 0.5 to about 4.5, preferably about 1.0 to about 2.0. The range of weaker acidic pH through basic pH is about 5.0 to about 9.0, preferably about 6.0 to about 7.5. Specifically, cellulose acetate phthalate, hydroxypropylmethylcellulose phthalate, hydroxypropylmethyl acetate succinate (Shin-Etsu Chemicals), methacrylic copolymers (Rhon-Pharma, Eudragit™ L-30D-55, L100-55, L100, S100, etc.), etc. can be mentioned as examples of the enteric coating agent. These materials are effective in terms of stability, even if they are directly used as enteric compositions.

For enteric coating, the conventional methods such as pan coating, fluidized-bed coating and spin coating can be employed. When the coating agent is a solution or dispersion containing water or an organic solvent, the spray coating method can also be used. The proportion of water or an organic solvent may for example be about 25 to about 99 weight %. The kind of organic solvent is not particularly critical. For example, alcohols (e.g. methanol, ethanol, isopropyl alcohol, etc.), ketones (e.g. acetone), and halogenated hydrocarbons (e.g. chloroform, dichloromethane, trichloromethane, etc.) can be employed.

The pharmaceutical composition of the present invention exhibits potent pharmacological activity with low toxicity so that it is useful as a medicament for prevention and treatment for, inter alia, angiogenesis-associated disease in mammals (e.g. mouse, rat, monkey, bovine, canine, human, etc.), said angiogenesis-associated disease including (1) inflammatory diseases such as rheumatoid arthritis, (2) diabetic retinopathy, and (3) benign and malignant tumors (e.g. gastric cancer, cancer of the esophagus, duodenal cancer, cancer of the tungue, pharyngeal cancer, brain tumors, neurilemoma, colorectal cancer, non-small-cell lung cancer, small cell carcinoma of the lung, hepatic carcinoma, renal cancer, cancer of the breast, biliary tract cancer, cancer of the pancreas, cancer of the prostate, cancer of the uterus, carcinoma of the uterine cervix, ovarian cancer, cancer of the urinary bladder, cancer of the skin, malignant melanoma, cancer of the thyroid, sarcomas of bone, hemangioma, hemangiofibroma, retinal sarcoma, cancer of the penis, solid tumors of childhood, Kaposi's sarcoma in AIDS, etc., inclusive of recurrencies and metastases to other organs). It is particularly useful when the dosage form of the present invention insures an effective blood concentration within the range not causing expression of the side effects of the active substance in prolonged time.

It is also advantageous, from the standpoint of stability, the pharmaceutical composition of the present invention is filled into capsule shells coated with the enteric coating agent as mentioned above for use as an enteric composition. As the capsule shell, for example, soft capsules (e.g. the product of R. P. Sealer) and hard gelatin capsules are used.

The liquid or solid pharmaceutical composition of the present invention can be administered orally in the per se known manner. In the case of the liquid form, it can be directly administered into the digestive tract via a catheter or sonde for oral administration or administered in the usual manner in the unit dosage form of a hard capsule or a soft capsule. In the case of the solid form, it can be administered orally as powders, capsules, tablets, or the like in the usual manner. It can also be redispersed in a suitable dispersion medium and administered in a liquid form. Taking a patient of breast cancer (body weight: 50 kg) as an example, the oral dose of the pharmaceutical composition of the present invention is about 1 mg to about 3 g/day, preferably about 10 mg to about 1 g/day, as a fumagillol derivative.

The pharmaceutical composition of the present invention enhances stability and oral absorption property of a fumagillol derivative and increases expression of pharmacological activity thereof, so that better assurance of therapeutic efficacy.

The dosage form of the present invention is stable and exhibits remarkable inhibiting activity on tumor growth and metastasis based on its antiangiogenesis activity in oral administration so that it can be used as clinically advantagiouse oral medicine.

The present invention is further explained in detail by the following examples, but the scope of the invention should not limit thereto.

EXAMPLE 1

6-O-(N-chloroacetylcarbamoyl)fumagillol (hereinafter referred to as compound A) was dissolved in Miglyol 812 [caprylic/capric acid triglyceride (Huls Aktiengesellschaft, Germany)] at a final concentration of 100 mg/ml (10% w/v) to provide a homogeneous solution.

EXAMPLE 2

Compound A was dissolved in Miglyol 829 [glyceryl succinate di(caprylate/caprate), Huls] at a final concentration of 100 mg/ml (10% w/v) to provide a homogeneous solution.

EXAMPLE 3

Compound A was dissolved in Miglyol 829 [glyceryl succinate di(caprylate/caprate), Huls] at a final concentration of 20 mg/ml (2% w/v) to provide a homogeneous solution.

EXAMPLE 4

Compound A was dissolved in oleic acid penta(tetra) glyceride (tradename PO-310, Sakamoto Yakuhin Kogyo Co. Ltd., Osaka) at a final concentration of 5 mg/ml (0.5% w/v) to provide a homogenous solution.

EXAMPLE 5

Behenic acid hexa(tetra)glyceride (tradename HB-310, Sakamoto Yakuhin Kogyo Co. Ltd., Osaka) (7.2 g) and stearic acid mono(tetra)glyceride (trade name MS-310, Sakamoto Yakuhin, Kogyo Co. Ltd., Osaka) (0.8 g) were melted at 85°0 C. Then, 1.0 g of compound A and 1.0 g of acrylic polymer (tradename HIVISWAKO 104, Wako Pure Chemical Industries Ltd., Osaka) were added and the mixture was stirred for dispersion at a constant temperature of 80° C. for 15 minutes. This molten mixture was dripped on a 15 cm (dia.) aluminum disk revolving at 2400 r.p.m. at a rate of 10 g/min. to provide spherical fine granules of 42/80 mesh (180–350 μm in diameter).

EXAMPLE 6

Behenic acid hexa(tetra)glyceride (tradename HB-310) (5.6 g) and stearic acid mono(tetra)glyceride (tradename MS-310) (2.4 g) were melted at 85° C. Then, 1.0 g of compound A and 1.0 g of acrylic polymer (tradename HIVISWAKO 104) were added and the mixture was stirred for dispersion at a constant temperature of 80° C. for 15 minutes. This molten mixture was dripped on a 15 cm (dia.) aluminum disk revolving at 2400 r.p.m. at a rate of 10 g/min. to provide spherical fine granules of 42/80 mesh (180–850 μm in diameter).

EXAMPLE 7

Behenic acid hexa(tetra)glyceride (tradename HB-310) (4.8 g) and stearic acid mono(tetra)glyceride (tradename MS-310) (3.2 g) were melted together at 85° C. Then, 1.0 g of compound A and 1.0 g of acrylic polymer (tradename HIVISWAKO 104) were added and the mixture was stirred for dispersion at a constant temperature of 80° C. for 15 minutes. This molten mixture was dripped on a 15 cm (dia.) aluminum disk revolving at 2400 r.p.m. at a rate of 10 g/min. to provide spherical fine granules of 42/80 mesh (180–350 μm in diameter).

EXAMPLE 8

A No. 0 gelatin capsule shell was filled with 0.6 ml of the solution obtained in Example 1. The surface of the resulting capsule was coated with hydroxypropylmethylcellulose phthalate (tradename HP-50, Shin-Etsu Chemicals) to provide an enteric capsule.

EXAMPLE 9

A No. 0 gelatin capsule shell was filled with 0.6 ml of the solution obtained in Example 2. The surface of the resulting capsule was coated with hydroxypropylmethylcellulose phthalate (tradename HP-50) to provide an enteric capsule.

EXAMPLE 10

A No. 0 gelatin capsule shell was filled with 0.6 ml of the solution obtained in Example 3. The surface of the resulting capsule was coated with hydroxypropylmethylcellulose phthalate (tradename HP-50) to provide an enteric capsule.

EXAMPLE 11

A No. 0 gelatin capsule shell was filled with 0.6 ml of the solution obtained in Example 4. The surface of the resulting capsule was coated with hydroxypropylmethylcellulose phthalate (tradename HP-50) to provide an enteric capsule.

EXAMPLE 12

A soft capsule shell (50 val, R.P. Sealer Co.) was filled with 0.8 ml of the solution obtained in Example 1. The surface of the resulting capsule was coated with hydroxypropylmethylcellulose phthalate (tradename HP-50) to provide an enteric capsule.

EXAMPLE 13

A soft capsule shell (50 val, R.P. Sealer Co.) was filled with 0.8 ml of the solution obtained in Example 2. The surface of the resulting capsule was coated with hydroxypropylmethylcellulose phthalate (tradename HP-50) to provide an enteric capsule.

EXAMPLE 14

A soft capsule shell (50 val, R.P. Sealer Co.) was filled with 0.8 ml of the solution obtained in Example 3. The surface of the resulting capsule was coated with hydroxypropylmethylcellulose phthalate (tradename HP-50) to provide an enteric capsule.

EXAMPLE 15

A soft capsule shell (50 val, R.P. Sealer Co.) was filled with 0.8 ml of the solution obtained in Example 4. The surface of the resulting capsule was coated with hydroxypropylmethylcellulose phthalate (tradename HP-50) to provide an enteric capsule.

EXAMPLE 16

300 mg of the fine granules obtained in Example 5 was filled in a No. 1 gelatin capsule shell. The surface of the resulting capsule was coated with hydroxypropylmethylcellulose phthalate (tradename HP-50) to provide an enteric capsule.

EXAMPLE 17

300 mg of the fine granules obtained in Example 6 was filled in a No. 1 gelatin capsule shell. The surface of the resulting capsule was coated with hydroxypropylmethylcellulose phthalate (tradename HP-50) to provide an enteric capsule.

EXAMPLE 18

300 mg of the fine granules obtained in Example 7 was filled in a No. 1 gelatin capsule shell. The surface of the resulting capsule was coated with hydroxypropylmethylcellulose phthalate (tradename HP-50) to provide an enteric capsule.

EXAMPLE 19

The fine granules obtained in Example 5 were loaded into a spiral flow coating apparatus (Freund Industrial Co., SFC-Labo) and spray-coated with a suspension of Enteric Eudragit L30D-55 (methacrylic copolymer LD, Rhön-Pharma) containing polyethylene glycol 6000, talc, titanium dioxide, and polysorbate 80 (Rheodol TW-0120), sieved, and dried in vacuum at 42° C. for about 18 hours to provide enteric fine granules.

EXAMPLE 20

The fine granules obtained in Example 6 were treated in the same manner as in Example 18 to provide enteric fine granules.

EXAMPLE 21

The fine granules obtained in Example 7 were treated in the same manner as in Example 18 to provide enteric fine granules.

EXAMPLE 22

Enteric coated granules containing compound A was prepared as follows:

(1) Preparation of compound A-containing granules

Formula:

| | | |
|---|---|---|
| Sugar Spheres NF | 110.0 | mg |
| Compound A | 52.4 | mg |

-continued

| (1) Preparation of compound A-containing granules | | |
|---|---|---|
| Formula: | | |
| Sucrose NF | 59.8 | mg |
| Starch NF | 36.4 | mg |
| Low-Substituted Hydroxypropyl Cellulose NF (L-HPC) | 40.0 | mg |
| Hydroxypropyl Cellulose NF (HPC-L) | 1.4 | mg |
| Ethanol | 0.07 | mg |
| Total | 300.0 | mg |

Sugar spheres were coated with a mixture of compound A, sucrose, starch and L-HPC by means of spraying HPC-L ethanol solution in a centrifugal fluid-bed granulator (CF-1000S, Freunt Co.). The resultant wet granules were dried in a vacuum oven at about 40° C. for about 18 hours, and then sieved and classified by size to 500 to 1250 μm granules.

| (2) Preparation of enteric coated granules | | |
|---|---|---|
| Formula: | | |
| Compound A-containing granules | 300.0 | mg |
| Hydroxypropylmethylcellulose phthalate (HPMCP) | 40.9 | mg |
| Ethanol | 1.0 | ml |
| Total | 340.9 | mg |

The granules obtained in the (1) above were coated with HPMCP ethanol solution in a spiral flow type coating machine (SFC-Labo, Freunt Co.), and sieved.

EXPERIMENTAL EXAMPLE 1

Tumor-bearing mice were provided by transplanting 1×10⁵ Colon 26 cancer cells/animal in the flank of female 10-week-old BALB/c mice (Charles River Japan). These tumor-bearing mice were divided into 4 groups and about 0.2 ml of either Miglyol 812 or a solution of compound A in Miglyol 812 (sample solution) was orally administered once daily from day 7 to day 20 following transplantation. On day 21, the tumor mass at the transplantation site was excised and weighed, and the tumor weight ratio relative to the untreated control group (T/C) was calculated. The results are shown in Table 1. In addition, the tumor colonies metastasized to the lungs were counted and the median value in each group was compared with that in the untreated control group (T/C). The results are shown in Table 2. The results indicate potent and dose-dependent effect of compound A on tumor growth inhibition and tumor metastasis inhibition.

TABLE 1

| | Dosage of Compound A (mg/kg) | Number of subjects | T/C (%) |
|---|---|---|---|
| Untreated control | | 10 | 100 |
| Miglyol 812 | 0 | 5 | 84 |
| Sample solution | 25 | 4 | 34 |
| | 50 | 5 | 21 |

TABLE 2

| | Dosage of Compound A (mg/kg) | Number of subjects | T/C (%) |
|---|---|---|---|
| Untreated control | | 10 | 100 |
| Miglyol 812 | 0 | 5 | 124 |
| Sample solution | 25 | 4 | 71 |
| | 50 | 5 | 52 |

EXPERIMENTAL EXAMPLE 2

Famotidine (Sigma) was administered subcutaneously to SD rats fasted overnight (dose; 10 mg/kg). One hour after administration, a methylcellulose suspension containing compound A was administered orally (dose; 100 mg/kg). Blood was serially drawn from the caudal vein to determine the plasma concentration of metabolites. As a control experiment, a similar compound A-containing suspension was administered to rats which is not administered famotidine. The results are shown in Table 3. As a result, a marked increase in absorption of compound A was found in the famotidine-treated group in which the intragastric pH level was elevated.

TABLE 3

| | Plasma concentration of metabolite (ng/ml) | | | | |
|---|---|---|---|---|---|
| | Time (min.) | | | | |
| | 5 | 10 | 15 | 30 | 60 |
| Untreated | 15.7 ± 1.6 | 17.3 ± 4.9 | 15.6 ± 1.6 | 5.8 ± 3.6 | 0 |
| Pretreated with famotidine | 92.9 ± 71.9 | 212.0 ± 41.7 | 210.4 ± 69.0 | 134.2 ± 29.0 | 105.9 ± 9.9 |

EXPERIMENTAL EXAMPLE 3

To SD rats fasted overnight, the solution of compound A in Miglyol 812 obtained in Example 3 was administered orally (dose; 100 mg/kg). Blood was collected from the caudal vein periodicaly to determine the plasma concentration of metabolite. The results are shown in Table 4. As a control experiment, a compound A-containing methylcellulose suspension was similarly administered. As a result, a marked increase in absorption of compound A was found in the group administered with the Miglyol solution.

TABLE 4

| | Plasma concentration of metabolite (ng/ml) | | | | |
|---|---|---|---|---|---|
| | Time (min.) | | | | |
| | 5 | 10 | 15 | 30 | 60 |
| Suspension | 15.7 ± 1.6 | 17.3 ± 4.9 | 15.6 ± 1.6 | 5.8 ± 3.6 | 0 |
| Solution of Example 3 | 17.7 ± 1.5 | 20.4 ± 1.6 | 16.7 ± 2.2 | 15.6 ± 1.8 | 30.3 ± 4.6 |

What is claimed is:

1. A method for treating or preventing angiogenesis associated diseases which comprises orally administering a pharmaceutical composition comprising a fumagillol derivative of the formula:

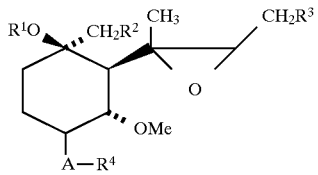

wherein $R^1$ represents hydrogen, $R^2$ represents halogen, $N(O)_m R^5 R^6$, $N^+ R^5 R^6 R^7 . X^-$, $S(O)_n R^5$, or $S^+ R^5 R^6 . X^-$ (wherein $R^5$, $R^6$, and $R^7$ respectively represent an optionally substituted hydrocarbon group or heterocyclic group, $X^-$ represents a counter anion, m represents an integer of 0 or 1; n represents an integer of 0–2; $R^5$ and $R^6$ may taken together with the adjacent nitrogen or sulfur atom to form an optionally condensed nitrogen- or sulfur-containing heterocyclic group which may be substituted), or $R^1$ and $R^2$ together represent a chemical bond; $R^3$ represents an optionally substituted 2-methyl-1-propenyl or isobutyl group; A represents O or $NR^8$ ($R^8$ represents hydrogen, an optionally substituted 2-methyl-1-propenyl or isobutyl group, or an optionally substituted aryl group); $R^4$ represents hydrogen, an optionally substituted hydrocarbon group, or an optionally substituted acyl group; or a salt thereof and a fatty acid alcohol ester, to a patient in need thereof.

2. The method as claimed in claim 1, wherein the pharmaceutical composition is coated with enteric materials.

3. The method as claimed in claim 1, wherein the fumagillol derivative is dissolved or dispersed in the fatty acid alcohol ester.

4. The method as claimed in claim 1, wherein the fumagillol derivative is about 0.001% to about 50% (w/v) relative to the fatty acid alcohol ester.

5. The method as claimed in claim 1, wherein the fatty acid alcohol ester is a fatty acid ester of glycerol or polyglycerol.

6. The method as claimed in claim 5, wherein the fatty acid ester of glycerol is a fatty acid triglyceride.

7. The method as claimed in claim 6, wherein the fatty acid triglyceride is a triglyceride of saturated $C_{6-22}$ fatty acid.

8. The method as claimed in claim 1, wherein the composition is a finely divided powder having a particle diameter of about 0.1 μm to about 10 mm.

9. The method as claimed in claim 5, wherein the pharmaceutical composition is one produced by drying a suspension comprising the fumagillol derivative shown in claim 5, a fatty acid alcohol ester and an emulsifier.

10. The method as claimed in claim 1, wherein the composition further comprises a gastric acid secretion.

11. The method as claimed in claim 1, wherein the composition further comprises an antacid.

12. The method as claimed in claim 1, wherein the composition further comprises a gastric acid secretion inhibitor and an antacid.

13. The method as claimed in claim 1, wherein $R^1$ and $R^2$ together represent a chemical bond or $R^1$ represents hydrogen with $R^2$ represents $N(O)_m R^5 R^6$, $N^+ R^5 R^6 R^7 . X^-$, $S(O)_n R^5$, or $S^+ R^5 R^6 . X^-$ (where each symbol has the same meaning defined in claim 1); A represents O or NH; $R^3$ represents an optionally substituted 2-methyl-1-propenyl or isobutyl group; and $R^4$ represents hydrogen or an optionally substituted carbamoyl group.

14. The method as claimed in claim 13, wherein $R^1$ and $R^2$ together represent a chemical bond.

15. The method as claimed in claim 13, wherein A represents O; $R^3$ represents a 2-methyl-1-propenyl or isobutyl group that may be substituted by hydroxy or dialkylamino; and $R^4$ represents carbamoyl substituted by $C_{1-6}$ alkyl or halo-$C_{1-6}$ alkanoyl.

16. The method as claimed in claim 1, wherein the fumagillol derivative is 6-O-(N-chloroacetylcarbamoyl)-fumagillol.

17. The method as claimed in claim 1, wherein the fumagillol derivative is 4-(N'-chloroacetylureido)-2-(1,2-epoxy-1,5-dimethyl-4-hyxenyl)-1-) 1,3-dihydrobenzo thiophen-2-ylio)methyl-3-methoxycyclohexanol chloride.

18. The method as claimed in claim 1, wherein the composition comprises 6-O-(N-chloroacetylcarbamoyl)-fumagillol or salt thereof and a triglyceride of saturated $C_{6-22}$ fatty acid.

19. The method as claimed in claim 1, wherein the composition comprises about 5 to about 30% (w/v) of 6-O-(N-chloroacetylcarbamoyl)fumagillol or a salt thereof relative to a triglyceride of saturated $C_{6-22}$ fatty acid.

20. The method as claimed in claim 9, wherein the composition is one produced by drying a suspension comprising 6-O-(N-chloroacetylcarbamoyl)fumagillol or a salt thereof, a triglyceride of saturated $C_{6-22}$ fatty acid, and an emulsifier.

21. The method as claimed in claim 1, wherein the composition is enteric-coated preparation.

22. The method as claimed in claim 1, wherein the enteric-coated preparation is a capsule.

23. A method for treating or preventing angiogenesis-associated diseases which comprises orally administering a pharmaceutical composition comprising a fumagillol derivative of the formula:

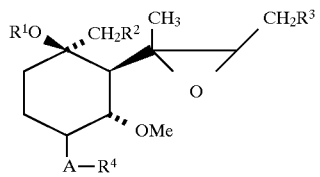

wherein $R^1$ represents hydrogen, $R^2$ represents halogen, $N(O)_m R^5 R^6$, $N^+ R^5 R^6 R^7 . X^-$, $S(O)_n R^5$, or $S^+ R^5 R^6 . X^-$ (wherein $R^5$, $R^6$, and $R^7$ respectively represent an optionally substituted hydrocarbon group or heterocyclic group, $X^-$ represents a counter anion, m represents an integer of 0 or 1; n represents an integer of 0–2; $R^5$ and $R^6$ may taken together with the adjacent nitrogen or sulfur atom to form an optionally condensed nitrogen- or sulfur-containing heterocyclic group which may be substituted), or $R^1$ and $R^2$ together represent a chemical bond; $R^3$ represents an optionally substituted 2-methyl-1-propenyl or isobutyl group; A represents O or $NR^8$ ($R^8$ represents hydrogen, an optionally substituted 2-methyl-1-propenyl or isobutyl group, or an optionally substituted aryl group); $R^4$ represents hydrogen, an optionally substituted hydrocarbon group, or an optionally substituted acyl group; or a salt thereof and a fatty acid alcohol ester, and a gastric acid secretion-inhibitor to a patient in need thereof.

24. A method for treating or preventing angiogenesis-associated diseases which comprises orally administering a pharmaceutical composition comprising a fumagillol derivative of the formula:

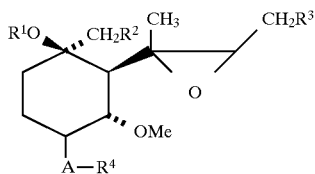

wherein $R^1$ represents hydrogen, $R^2$ represents halogen, $N(O)_mR^5R^6$, $N^+R^5R^6R^7.X^-$, $S(O)_nR^5$, or $S^+R^5R^6.X^-$ (wherein $R^5$, $R^6$, and $R^7$ respectively represent an optionally substituted hydrocarbon group or heterocyclic group, $X^-$ represents a counter anion, m represents an integer of 0 or 1; n represents an integer of 0–2; $R^5$ and $R^6$ may taken together with the adjacent nitrogen or sulfur atom to form an optionally condensed nitrogen- or sulfur-containing heterocyclic group which may be substituted), or $R^1$ and $R^2$ together represent a chemical bond; $R^3$ represents an optionally substituted 2-methyl- 1-propenyl or isobutyl group; A represents O or $NR^8$ ($R^8$ represents hydrogen, an optionally substituted 2-methyl-1 -propenyl or isobutyl group, or an optionally substituted aryl group); $R^4$ represents hydrogen, an optionally substituted hydrocarbon group, or an optionally substituted acyl group; or a salt thereof and a fatty acid alcohol ester, and an antacid to a patient in need thereof.

25. A method for treating or preventing angiogenesis-associated diseases which comprises orally administering, a pharmaceutical composition comprising a fumagillol derivative of the formula:

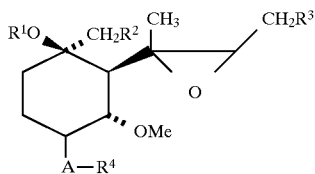

wherein $R^1$ represents hydrogen, $R^2$ represents halogen, $N(O)_mR^5R^6$, $N^+R^5R^6R^7.X^-$, $S(O)_nR^5$, or $S^+R^5R^6.X^-$ (wherein $R^5$, $R^6$, and $R^7$ respectively represent an optionally substituted hydrocarbon group or heterocyclic group, $X^-$ represents a counter anion, m represents an integer of 0 or 1; n represents an integer of 0–2; $R^5$ and $R^6$ may taken together with the adjacent nitrogen or sulfur atom to form an optionally condensed nitrogen- or sulfur-containing heterocyclic group which may be substituted), or $R^1$ and $R^2$ together represent a chemical bond; $R^3$ represents an optionally substituted 2-methyl-1-propenyl or isobutyl group; A represents O or $NR^8$ ($R^8$ represents hydrogen, an optionally substituted 2-methyl- 1-propenyl or isobutyl group, or an optionally substituted aryl group); $R^4$ represents hydrogen, an optionally substituted hydrocarbon group, or an optionally substituted acyl group; or a salt thereof and a fatty acid alcohol ester, a gastric acid secretion-inhibitor and an antacid to a patient in need thereof.

26. The method of claim 23, wherein the pharmaceutical composition is administered after the administration of the gastric acid secretion inhibitor.

27. The method of claim 24, wherein the pharmaceutical composition is administered after the administration of the antacid.

28. The method of claim 25, wherein the pharmaceutical composition is administered after the administration of the gastric acid secretion inhibitor and the antacid.

* * * * *